(12) United States Patent
Lee

(10) Patent No.: US 9,031,660 B2
(45) Date of Patent: May 12, 2015

(54) EYE IMPLANT APPARATUS AND UPDATE SYSTEM FOR THE SAME

(71) Applicant: Neurotech Limited, Hong Kong (CN)

(72) Inventor: Winghong Lee, Hong Kong (CN)

(73) Assignee: Neurotech Limited, Central, Hong Kong (CN)

( * ) Notice: Subject to any disclaimer, the term of this patent is extended or adjusted under 35 U.S.C. 154(b) by 0 days.

(21) Appl. No.: 13/854,228

(22) Filed: Apr. 1, 2013

(65) Prior Publication Data

US 2013/0261700 A1   Oct. 3, 2013

(30) Foreign Application Priority Data

Apr. 1, 2012   (CN) .......................... 2012 1 0094397

(51) Int. Cl.
*A61N 1/36* (2006.01)
*A61N 1/372* (2006.01)
*A61N 1/08* (2006.01)
*A61N 1/378* (2006.01)

(52) U.S. Cl.
CPC .............. *A61N 1/36046* (2013.01); *A61N 1/08* (2013.01); *A61N 1/3787* (2013.01); *A61N 1/36071* (2013.01); *A61N 1/37264* (2013.01)

(58) Field of Classification Search
USPC ....................................... 607/29, 33; 623/4.1
See application file for complete search history.

(56) References Cited

U.S. PATENT DOCUMENTS

| 2003/0195581 A1* | 10/2003 | Meadows et al. ................ 607/29 |
| 2010/0042209 A1* | 2/2010 | Guarnieri ....................... 623/4.1 |
| 2011/0248671 A1* | 10/2011 | Dos Santos et al. .......... 320/108 |

* cited by examiner

*Primary Examiner* — Carl Layno
*Assistant Examiner* — Jon Eric C Morales
(74) *Attorney, Agent, or Firm* — Rosenberg, Klein & Lee

(57) ABSTRACT

The present disclosure discloses an apparatus to be implanted in eyes, including: a configuration memory used for storing signal parameter configuration; a signal generator connected to the configuration memory and used for generating stimulating signals according to the signal parameter configuration in the configuration memory; electrodes connected to the signal generator and contact with outer surface of eye ball after implanted; a communication assembly connected to the configuration memory and used for receiving the signal parameter configuration, storing the received signal parameter configuration in the configuration memory; and a power supply connected to the configuration memory, signal generator and communication assembly, used for providing power. An update system for the apparatus is also disclosed. By using the above apparatus and update system, when it needs to change waveform parameter of stimulating signals, there is no need to take the apparatus out, reducing harm on human body and improving safety.

17 Claims, 5 Drawing Sheets

EYE IMPLANT APPARATUS AND UPDATE SYSTEM FOR THE SAME

FIELD OF THE INVENTION

The present disclosure relates to medical equipment, more particularly, to an eye implant apparatus and an update system for the same.

BACKGROUND OF THE INVENTION

Opticatrophy is a kind of formation change that all optic nerves become thinner. The change is caused by pathological changes on retinal ganglion cells and axon caused by any disease. The opticatrophy generally occurs on the retinal ganglion axon located between the retina and the lateral geniculate. The reasons may be various, while common reasons include ischemia, inflammation, stress, wound and demyelinating disease.

Conventionally, electrical stimulating apparatus are implanted in eyes of patients to prevent and treat the opticatrophy by stimulating the optic nerves. In the conventional technology, after the electrical stimulating apparatus being implanted, continuous electric stimulation will be applied on the optic nerves to treat the opticatrophy.

In a conventional apparatus, waveform parameter of stimulating signals for stimulating eye need preset, that is, set before implantation, and stored as signal parameter configuration. The signal parameter configuration cannot be modified after being written in the apparatus. So, after the conventional apparatus being implanted in eyes, it generates electric signals having fixed waveform parameter according to the preset signal parameter configuration. If the patient condition changes, the stimulating signals need to be modified. The old apparatus will be taken out and new apparatus will be implanted to continue the treatment. Since the patient needs anaesthesia and the apparatus needs fixed when implanting or taking out the apparatus, it may cause damage on human body, so the conventional eye implant apparatus has very low safety.

SUMMARY OF THE INVENTION

It is an object of the present invention to provide an eye implant apparatus and an update system for the apparatus.

An apparatus to be implanted in eyes, including: a configuration memory configured for storing signal parameter configuration; a signal generator connected to the configuration memory and configured for generating stimulating signals according to the signal parameter configuration in the configuration memory; an electrode connected to the signal generator and contacting an outer surface of eye ball after the electrode is implanted; a communication assembly connected to the configuration memory and configured for receiving the signal parameter configuration, storing the received signal parameter configuration in the configuration memory; and a power supply connected to the configuration memory, signal generator and communication assembly, configured for providing power.

In a preferred embodiment, the communication assembly includes: an antenna; a signal processing module connected to the antenna and configured for decoding a received radio wave signal to the signal parameter configuration; and a key memory connected to the signal processing module and configured for storing a communication key; wherein the communication assembly is connected to the configuration memory via the signal processing module.

In a preferred embodiment, the power supply includes a power adjusting module, and the power supply is connected to the configuration memory, the signal generator and the communication assembly via the power adjusting module, the power supply is configured for AC-DC converting and voltage stabilization.

In a preferred embodiment, the power supply further includes a power receiving module connected to the power adjusting module and antenna, the power receiving module is configured for obtaining power through the antenna.

In a preferred embodiment, the antenna includes a receiving coil, and the power supply receives radio energy through the receiving coil.

In a preferred embodiment, the power supply obtains electrical power by utilizing at least one way selected from human temperature, muscle movement and receiving radio wave.

In a preferred embodiment, the signal parameter configuration includes at least one waveform parameter selected from amplitude, waveform function, period and duty ratio of the stimulation signal.

An update system for the apparatus to be implanted in eyes, including: an external update device; and an eye implant apparatus including: an antenna; a signal processing module connected to the antenna and configured for decoding the received radio wave signals to the signal parameter configuration; a key memory connected to the signal processing module and configured for storing communication key; the communication assembly is connected to the configuration memory via the signal processing module; the external update device is configured for sending the signal parameter configuration to the communication assembly of the eye implant apparatus through a wireless channel; the communication assembly of the eye implant apparatus is also configured for receiving the signal parameter configuration, and updating the signal parameter configuration in the configuration memory.

the external update device is used for sending the signal parameter configuration to the communication assembly of the eye implant apparatus through wireless channel; the communication assembly of the eye implant apparatus is also used for receiving the signal parameter configuration, and storing the signal parameter configuration in the configuration memory.

In a preferred embodiment, the communication assembly includes: an antenna; a signal processing module connected to the antenna and configured for decoding a received radio wave signal to the signal parameter configuration; and a key memory connected to the signal processing module and configured for storing a communication key; wherein the external update device is further configured for encrypting the signal parameter configuration according to preset communication key.

Since communication assembly is included in the apparatus, if it needs to adjust the waveform parameter of the signals generated by the apparatus implanted in the eye according to patient's condition, the signal parameter configuration will be encoded by the externals devices and sent to the communication assembly of the apparatus implanted in the eye through wireless channel. The communication assembly receives and decodes the signal parameter configuration, and stores in the configuration memory. The signal generator generates adjusted signals to stimulate the optic nerves according to the refreshed signal parameter configuration. As a result, when it needs to change waveform parameter of stimulating signals,

DETAILED DESCRIPTION OF THE EMBODIMENTS

The invention will be described in detail with the following embodiments and drawings.

Figure 1:
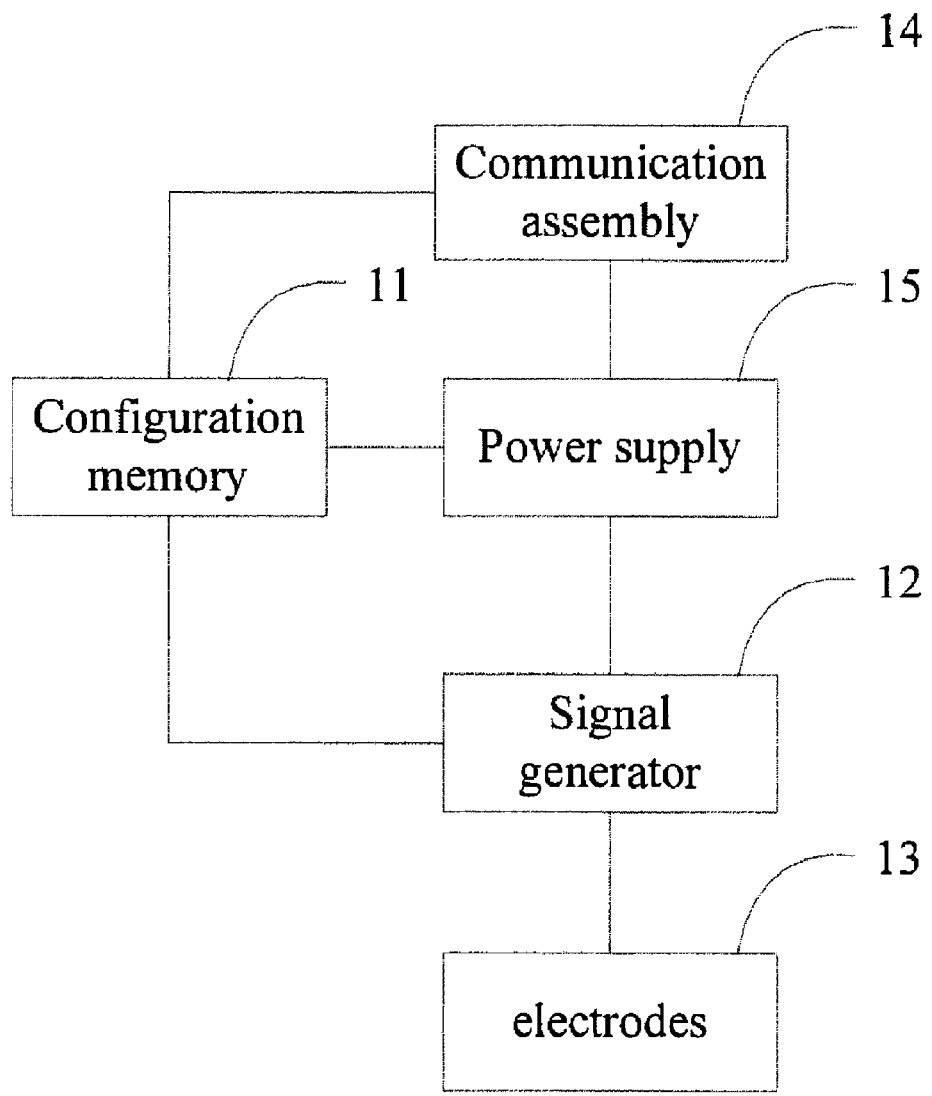
FIG. 1 is a block diagram of an eye implant apparatus according to an embodiment.

Referring to FIG. 1, in one embodiment, an apparatus 10 to be implanted in an eye includes a configuration memory 11, a signal generator 12 connected to the configuration memory 11, electrodes 13 connected to the signal generator 12 and contacting an outer surface of eye ball, a communication assembly 14 connected to the configuration memory 11, a power supply 15 connected to the configuration memory 11, signal generator 12 and communication assembly 14.

The configuration memory 11 is used for storing signal parameter configuration. The signal parameter configuration may be stored in the configuration memory 11 as files or data stream. The signal parameter configuration includes at least one waveform parameter selected from amplitude, waveform function, period and duty ratio of the stimulation signal. The configuration memory 11 may be a flash memory.

The signal generator 12 is used for generating a stimulating signal according to the signal parameter configuration stored in the configuration memory 11. The signal generator 12 may include logic circuit, which can generate a plurality of signals according to the preset waveform parameters. The signal generator 12 reads signal parameter configuration from the configuration memory 11 and obtains waveform parameters of signals ready to be generated, such as amplitude, waveform function, period and duty ratio, and generates corresponding signals according to the obtained waveform parameters.

The electrodes 13 contact the outer surface of the eye ball for conducting electrical signals to stimulate the optic nerves. More preferably, electrodes 13 are made of gold. Gold has a low resistivity and an excellent conductivity, such that it can reduce power loss in stimulation. Gold also has stable chemical property and is hard to be oxidized, such that it is biocompatible to the human body when the eye ball contacts electrodes 13 for a long time. The electrodes can be an extension out of a main chip, or one of the electrodes can be attached to the chip.

The communication assembly 14 is used for receiving the signal parameter configuration and storing the received signal parameter configuration in the configuration memory 11. After receiving radio wave signals, the communication assembly 14 decodes the radio wave signals to the signal parameter configuration and stores in the configuration memory 11.

Figure 2:
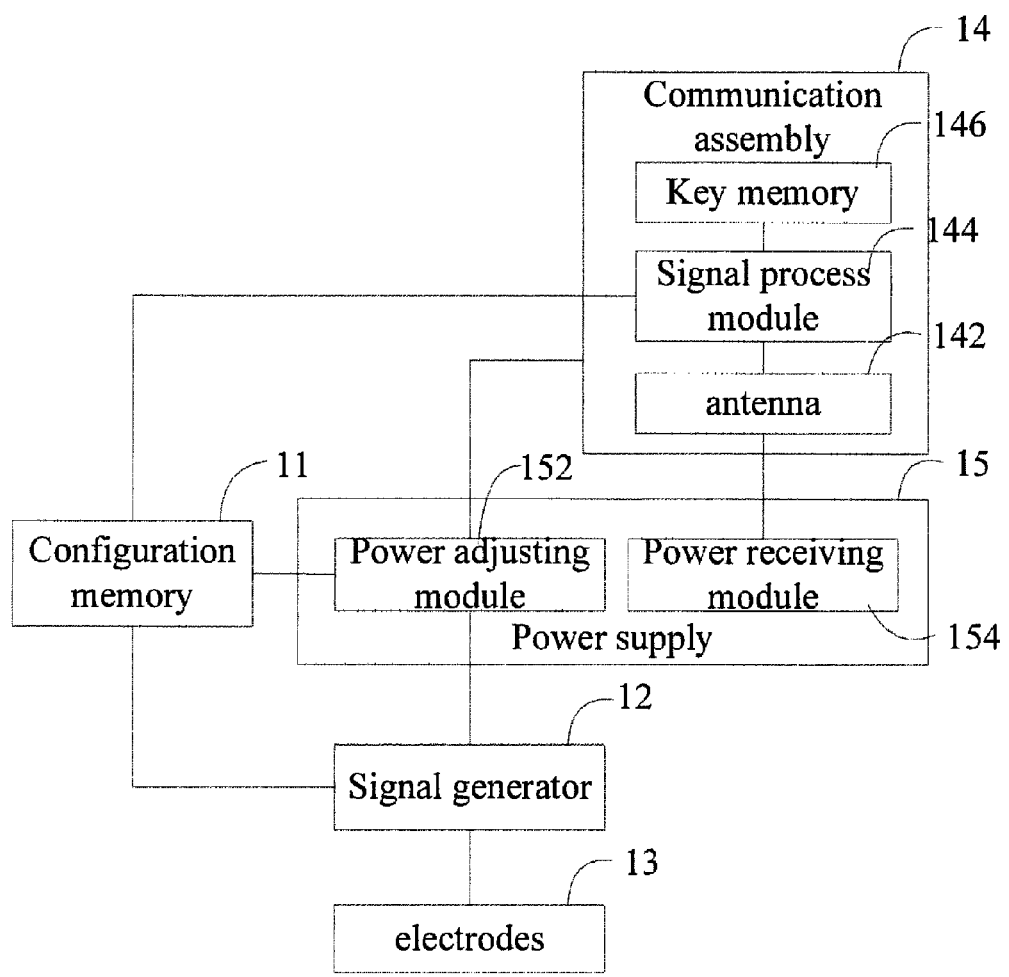
FIG. 2 is a block diagram of an eye implant apparatus according to another embodiment.

In one embodiment, as shown in FIG. 2, the communication assembly 14 includes an antenna 142, a signal processing module 144 connected to the antenna 142 and used for decoding the received radio wave signals to the signal parameter configuration, a key memory 146 connected to the signal processing module 144 and used for storing communication key. The communication assembly 14 is connected to the configuration memory 11 via the signal processing module 144.

For the communication assembly 14, it is a two way communication. Through the communication assembly 14, the implantable apparatus 10 can receive information such as the update information from the external device 30. The implantable apparatus 10 can also send back information to the external device 30. One of the important feature is to control the amount of power transfer through the wireless mean. The implantable apparatus can check whether it receives excess power or not enough power from the power supply 15. It can then send back "power control" information to the external device 30 to either increase or decrease the amount of power transmitted to the implantable apparatus 10. In this case, it can optimize the power transfer and to avoid excess power transfer which will lead to overheat of the surrounding muscle or tissues.

The antenna 142 receives the radio wave signals and sends the radio wave signals to the signal processing module 144. The signal processing module 144 firstly decodes the radio wave signals to ciphertext according to preset channel coding function, then it obtains the communication key from the key memory 146 and decodes the ciphertext to the signal parameter configuration according to the communication key, lastly, it stores the signal parameter configuration in the configuration memory 11. The communication key may be device identification or a preset fingerprinting code. The device identification is written in the key memory 146 when the apparatus 10 leaves the factory and the communication key is unique in global. The fingerprinting code will be written in the key memory 146 when the apparatus 10 is ready to be implanted in the patient's eye, so as to identify patients.

By adding the key memory 146, the communication assembly 14 can build an encrypted communication with the external devices, such that it guarantees communication security between the communication assembly 14 and external devices, and prevents receiving error of the communication assembly 14 caused by multiple external devices broadcasting the signal parameter configuration at the same time.

The power supply 15 is used for providing power. The power supply 15 obtains electrical power from at least one way including utilizing human temperature, muscle movement and receiving radio wave. The power supply 15 may have a "power extraction part" that can extract power either from thermal, muscle contraction or radio wave. The way of obtaining electrical power from human temperature is achieved by setting thermoelectric cell. The thermoelectric cell obtains electrical power by utilizing temperature difference between the human body temperature and ambient temperature according to the "Zwiebel" effect. The way of obtaining electrical power from muscle movement is achieved by setting nano wire in the muscle of eyes and electrical power is obtained by bending the nano wire when the muscle moves.

In one embodiment, as shown in FIG. 2, the power supply 15 further includes a power adjusting module 152. The power supply 15 is connected to the configuration memory 11, signal generator 12 and communication assembly 14 via the power adjusting module 152. The power adjusting module 152 is used for AC-DC converting and voltage stabilization. For example, when the power supply 15 obtains electrical power from radio wave, the power adjusting module 152 will convert the received high frequency alternating current signal to direct current, in order to provide power for the configuration memory 11, signal generator 12 and communication assembly 14.

There are three types of power supply mentioned above, including wireless power, thermal power, and muscle contraction, the first and the last one are AC power sources, so that the power supply module consists of an AC-DC converter. However for thermal power, it is a DC output source, so we need only DC-DC converter. So module 152 can be a AC-DC rectifier or a DC-DC converter. Meanwhile, the antenna is only used for wireless power transfer. For thermal power and muscle movement, no antenna is needed and we need to have a connection mean to get the power from the thermal transducer and the mechanical device for muscle movement.

In the illustrated embodiment, as shown in FIG. 2, the power supply 15 further includes a power receiving module 154 connected to the power adjusting module 152 and antenna 142 for gaining power through the antenna 142.

Moreover, the antenna 142 has a receiving coil, through which the power supply 15 receives radio wave.

Figure 3:
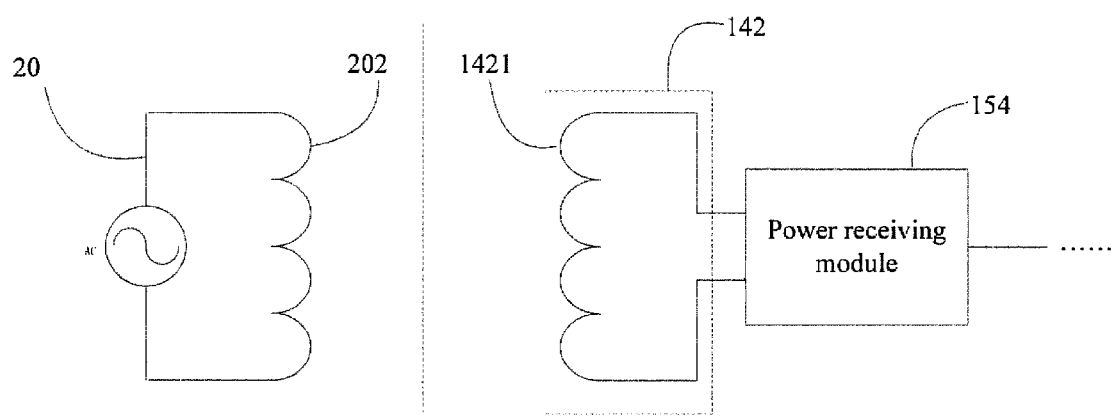
FIG. 3 is a schematic view of an antenna of the eye implant apparatus shown in FIG. 2.

Referring to FIG. 3, the external power supply device 20 has an emitting coil 202. The receiving coil 1421 couples with the emitting coil 202. The external power supply device 20 may be installed in an area near the eye ball, for example, on a glass frame, a glass arm, an eye pad or a hearing-aid. The external power supply device 20 sends electric magnetic wave to the receiving coil 1421 through the emitting coil 202. Because the receiving coil 1421 couples with the emitting coil 202, the power receiving module 154 gains electric power from the receiving coil 1421. If the energy of the external power supply device 20 is exhausted, there is no need to remove the apparatus 10, but to replace power source of the external power supply device 20. As a result, there is no need for the apparatus to carry power source, thus the size is smaller, and the life time is longer, making the patient more comfortable.

In alternative embodiments, in order to guarantee communication quality and transmitted power, the power receiving module 154 may have a high frequency receiving antenna independent from the communication assembly 14, such that the communication assembly 14 transmits data through low frequency channel, the power receiving module 154 transmits energy through high frequency channel, reducing interference from each other. However the data can also be transmitted through the same frequency channel using data modulation. Also the device can send back data to the external device using the same channel through back-scattering approach.

If it is necessary to adjust the waveform parameter of the signals generated by the apparatus implanted in the eye according to patient's condition, the signal parameter configuration will be encoded by the externals devices and sent to the communication assembly of the apparatus implanted in the eye through wireless channel. The communication assembly receives and decodes the signal parameter configuration, and stores in the configuration memory. The signal generator generates adjusted signals to stimulate the optic nerves according to the refreshed signal parameter configuration. As a result, when it needs to change waveform parameter of stimulating signals, there is no need to take the apparatus out, thus reducing harm on human body and improving safety.

In one embodiment, the apparatus 10 is integrated into an implantable chip. The whole apparatus 10 includes the implantable chip, the antenna, the electrodes, and the leads to the electrodes are enclosed by biocompatible material such as bio-compatible silicone and will be implanted at the surface of the eyeball, under the eye muscle. The apparatus 10 may be implanted in the bottom portion of the outer surface of the eye balls and located in the eyehole. The apparatus 10 is eclipse shaped and it has a plurality of electrodes contacting a plurality of optic nerves. When the apparatus 10 is in operation, the signal generator 12 may generate intermittent modulated waves with tunable duty ratio, for example, 1%~20%, tunable stimulation frequency, for example, 20~50 Hz, and tunable amplitude, for example, 1%~100%.

In another embodiment, the signal generator 12 has an amplitude threshold for limiting amplitude of the signal generated by the signal generator. If the signal parameter configuration stored in the configuration memory 11 is wrong (caused by human or decoding error), the signal generator 12 may generate large current and cause damage on the eyes. However, the amplitude threshold set in the signal generator 12 can limit the amplitude of the current generated by the signal generator 12, thus preventing damage on the eyes caused by wrong signal parameter configuration and improving safety.

Figure 4:
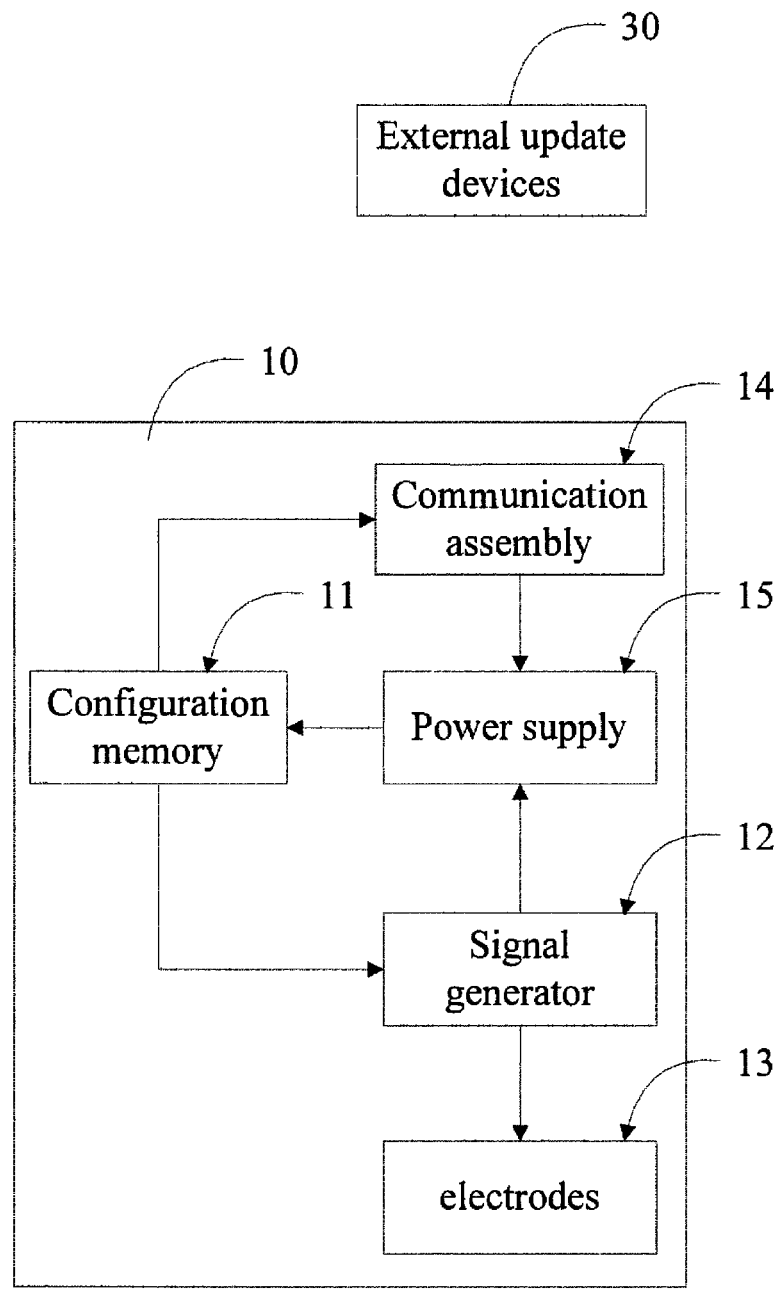
FIG. 4 is a block diagram of an update system for the eye implant apparatus according to an embodiment.

In one embodiment, shown in FIG. 4, an update system for the apparatus implanted in eyes includes external update device 30 and the above mentioned apparatus 10.

The apparatus 10 includes configuration memory 11, a signal generator 12 connected to the configuration memory 11, electrodes 13 connected to the signal generator 12, a communication assembly 14 connected to the configuration memory 11, a power supply 15 connected to the configuration memory 11, signal generator 12 and communication assembly 14.

The external update device 30 is used for sending the signal parameter configuration to the communication assembly 14 of the apparatus 10 through wireless channel. The communication assembly 14 of the apparatus 10 is also used for receiving the signal parameter configuration, and storing the signal parameter configuration in the configuration memory 11.

In the update system, the apparatus implanted in the eyes has communication assembly. If it is necessary adjust the waveform parameter of the signals generated by the apparatus implanted in the eye according to patient's condition, the signal parameter configuration will be coded by the externals devices and sent to the communication assembly of the apparatus implanted in the eye through wireless channel. The communication assembly receives and decodes the signal parameter configuration, and stores in the configuration memory. The signal generator generates adjusted signals to stimulate the optic nerves according to the refreshed signal parameter configuration. As a result, when it needs to change waveform parameter of stimulating signals, there is no need to take the apparatus out, reducing harm on human body and improving safety.

Figure 5:
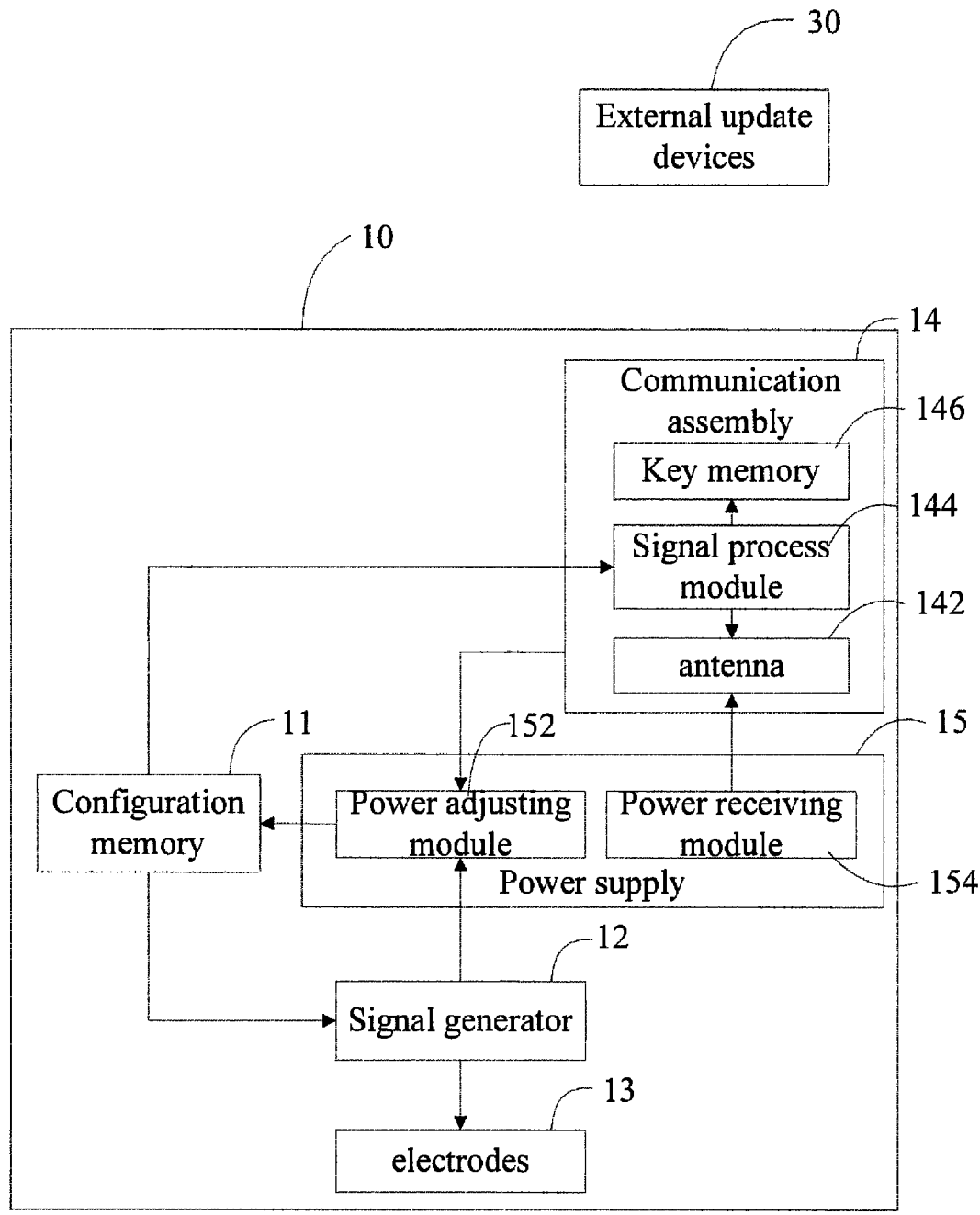
FIG. 5 is a block diagram of an update system for the eye implant apparatus according to another embodiment.

In one embodiment, shown in FIG. 5, the external update device 30 is further used for coding the signal parameter configuration according to preset communication key.

The communication assembly 14 includes an antenna 142, an signal processing module 144 connected to the antenna 142 and used for decoding the received wireless signal to the signal parameter configuration, a key memory 146 connected to the signal processing module 144 and used for storing communication key. The communication assembly is connected to the configuration memory 11 via the signal processing module 144.

By adding the key memory 146, the communication assembly 14 can build coded communication with external devices, such that guarantees communication security between the communication assembly 14 and external devices, preventing receive error of the communication assembly 14 caused by multiple external devices broadcasting the signal parameter configuration at the same time.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. An eye implant apparatus, comprising:
   a configuration memory configured for storing signal parameter configuration;
   a key memory connected to the signal processing module and configured for storing a pre-established communication key, the pre-established communication key including at least one of a globally unique device identification established at manufacture and a preset fingerprinting code established according to a patient identification;
   a signal generator connected to the configuration memory and configured for generating stimulating signals according to the signal parameter configuration in the configuration memory;
   an electrode connected to the signal generator and contacting an outer surface of an eye ball after the electrode is implanted, wherein the electrode is gold;
   a communication assembly connected to the configuration memory and the key memory and configured for receiving and decrypting the signal parameter configuration according to the communication key, storing the received signal parameter configuration in the configuration memory; and
   a power supply connected to the configuration memory, signal generator and communication assembly, the power supply being selectively configured for adjustably providing power responsive to a predetermined set of operational parameters and wherein the power supply is devoid of a battery.

2. The apparatus of claim 1, wherein the communication assembly comprises:
   an antenna;
   a signal processing module connected to the antenna and configured for decoding a received radio wave signal to the signal parameter configuration; and
   wherein the communication assembly is connected to the configuration memory via the signal processing module.

3. The apparatus of claim 2, wherein the power supply comprises a power adjusting module, and the power supply is connected to the configuration memory, the signal generator and the communication assembly via the power adjusting module, the power supply is configured for AC-DC converting and voltage stabilization.

4. The apparatus of claim 3, wherein the power supply further comprises a power receiving module connected to the power adjusting module and antenna, the power receiving module is configured for obtaining power through the antenna.

5. The apparatus of claim 4, wherein the antenna comprises a receiving coil, and the power supply receives radio energy through the receiving coil.

6. The apparatus of claim 1, wherein the power supply obtains electrical power by utilizing at least one way selected from human temperature, and muscle movement.

7. The apparatus as recited in claim 6, wherein the power supply obtains electrical power by muscle movement harnessed by a bendable nanowire disposed in contact therewith.

8. The apparatus as recited in claim 6, wherein the power supply further includes a thermoelectric cell obtaining power by temperature differential between the eyeball and an ambient temperature.

9. The apparatus of claim 1, wherein the signal parameter configuration comprises at least one waveform parameter selected from amplitude, waveform function, period and duty ratio of the stimulation signal.

10. The apparatus as recited in claim 1, wherein the apparatus is enclosed in a biocompatible material and the electrodes are formed of gold.

11. The apparatus as recited in claim 10, wherein the apparatus is enclosed in biocompatible silicone.

12. An update system for an eye implant apparatus, comprising:
    an external update device; and
    an eye implant apparatus comprising:
       an electrode contacting the outer surface of the eyeball, wherein the electrode is gold;
       a power supply devoid of a battery, the power supply being selectively configured for adjustably providing power to the eye implant apparatus responsive to muscle movement harnessed by a bendable nanowire disposed in contact therewith; and,
       a communication assembly including:
          an antenna;
          a signal processing module connected to the antenna and configured for decoding received radio wave signals to signal parameter configurations; and,
          a key memory connected to the signal processing module and configured for storing a pre-established communication key, the communication assembly is connected to a configuration memory via the signal processing module;
    the external update device is configured for sending encoded signal parameter configurations via radio wave signals to the communication assembly of the eye implant apparatus through a wireless channel; the communication assembly of the eye implant apparatus is also configured for receiving the signal parameter configuration, and updating the signal parameter configuration in the configuration memory.

13. The system of claim 12, wherein the external update device is further configured for encrypting the signal parameter configuration according to preset communication key.

14. The system as recited in claim 12, wherein the eye implant apparatus is enclosed in a biocompatible material and the electrodes are formed of gold.

15. The system as recited in claim 14, wherein the eye implant apparatus is enclosed in biocompatible silicone.

16. The system as recited in claim 12, wherein, the pre-established communication key includes at least one of a globally unique device identification established at manufacture and a preset fingerprinting code established according to a patient identification.

17. An update system for an eye implant apparatus, comprising:
    an external update device; and
    an eye implant apparatus comprising:
       an electrode contacting the outer surface of the eyeball, wherein the electrode is gold;
       a power supply devoid of a battery, the power supply being selectively configured for adjustably providing power to the eye implant apparatus responsive to a predetermined set of operational parameters, the power supply having a thermoelectric cell obtaining power by temperature differential between the eyeball and an ambient temperature; and,
a communication assembly including:
an antenna;
a signal processing module connected to the antenna and configured for decoding received radio wave signals to signal parameter configurations; and,
a key memory connected to the signal processing module and configured for storing a pre-established communication key, the communication assembly is connected to a configuration memory via the signal processing module;

the external update device is configured for sending encoded signal parameter configurations via radio wave signals to the communication assembly of the eye implant apparatus through a wireless channel; the communication assembly of the eye implant apparatus is also configured for receiving the signal parameter configuration, and updating the signal parameter configuration in the configuration memory.

* * * * *